United States Patent [19]

Abou-Sayed et al.

[11] 4,152,941
[45] May 8, 1979

[54] PROCESS FOR MEASURING THE FRACTURE TOUGHNESS OF ROCK UNDER SIMULATED DOWN-HOLE STRESS CONDITIONS

[75] Inventors: Ahmed S. Abou-Sayed; Arfon H. Jones, both of Salt Lake City, Utah

[73] Assignee: Terra Tek, Inc., Salt Lake City, Utah

[21] Appl. No.: 903,962

[22] Filed: May 8, 1978

[51] Int. Cl.² ............................................. G01N 3/12
[52] U.S. Cl. ......................................... 73/799; 73/804
[58] Field of Search .................... 73/88 E, 94, 37, 799, 73/804, 825; 166/250

[56] References Cited

U.S. PATENT DOCUMENTS 3,199,341  10/1965  Heuer, Jr. et al. ....................... 73/94
3,580,334  5/1971  Broussard et al. ................. 73/151 X Primary Examiner—Jerry W. Myracle
Attorney, Agent, or Firm—M. Reid Russell

[57] ABSTRACT

The present invention relates to a method for measuring the fracture toughness of rock as it would exhibit in its natural down-hole setting. Practicing the method of the present invention involves internally pressurizing a rock specimen while simultaneously exerting an increasing external horizontal stress thereon, raising simultaneously the internal pressure to maintain a desired relationship of exterior to interior pressures until the specimen fractures, which pressure, in relationship to the stress intensity factor and specimen geometry, provides the specimen fracture toughness as it would exist in a down-hole situation.

5 Claims, 8 Drawing Figures

| Test # | 2a (mm) | 2b (mm) | Height (mm) | Axial Stress (MPa) | Confining Pressure (MPa) | Pore Pressure (MPa) | Internal Pressure (MPa) | $K_{Ic}$ (MPa·mm) |
|---|---|---|---|---|---|---|---|---|
| 1 | 9.5 | 104 | 47 | 0.7 | 0.0 | 0.0 | 18.1 | 28.1 |
| 2 | 9.5 | 104 | 46 | 0.7 | 0.0 | 0.0 | 16.0 | 24.9 |
| 3 | 9.5 | 104 | 43 | 0.7 | 0.0 | 0.0 | 15.5 | 24.1 |
| 4 | 9.5 | 104 | 104 | 0.7 | 0.0 | 0.0 | 16.7 | 26.1 |
| 5 | 9.5 | 104 | 104 | 0.7 | 0.0 | 0.0 | 14.7 | 23.0 |
| 6 | 9.5 | 104 | 104 | 7.0 | 0.0 | 0.0 | 14.2 | 22.2 |
| 7 | 9.5 | 104 | 104 | 7.0 | 0.0 | 0.0 | 18.5 | 28.8 |
| 8 | 9.5 | 104 | 104 | 7.0 | 0.0 | 0.0 | 16.7 | 26.1 |
| 9 | 9.5 | 104 | 104 | 7.0 | 7.0 | 7.0 | 17.8 | 27.3 |
| 10 | 9.5 | 104 | 104 | 7.0 | 7.0 | 7.0 | 15.5 | 23.8 |
| 11 | 9.5 | 104 | 104 | 7.0 | 7.0 | 7.0 | 16.7 | 25.6 |
| 12 | 9.5 | 104 | 104 | 7.0 | 7.0 | 7.0 | 17.8 | 27.4 |
| 13 | 9.5 | 64 | 64 | 6.0 | 6.0 | 0.0 | 48.0 | 43.3 |
| 14 | 9.5 | 64 | 64 | 6.9 | 6.9 | 0.0 | 54.8 | 48.5 |
| 15 | 9.5 | 64 | 64 | 6.3 | 6.3 | 0.0 | 50.1 | 44.8 |

PROCESS FOR MEASURING THE FRACTURE TOUGHNESS OF ROCK UNDER SIMULATED DOWN-HOLE STRESS CONDITIONS

BRIEF DESCRIPTION OF THE INVENTION

1. Field of the Invention

This invention relates to methods for measuring the fracture toughness of a rock specimen in a laboratory setting that simulates the stress conditions acting on that specimen as they would exist in a down-hole setting.

2. Setting of the Invention

With our country's increasing need to become less dependent upon foreign oil sources it is increasingly imperative that a maximum yield be obtained from each oil or gas field and even each well within a particular field. One approach to increasing well yield, that has in recent times met with success, particularly in recovering natural gas reserves located in low permeability sandstone reservoirs, or the like, has been the fracturing of such wells for increasing production. Where such fracturing is appropriate the increased production from a well will generally more than offset the cost of such fracturing. However, where a well is not suited for fracturing, due to the type or conditions of the rock wherein the well is drilled, such fracturing may not be economically feasible and therefore should not be undertaken. The present invention, in a laboratory setting provides for a determination of the fracture toughness of a rock specimen that it would exhibit in a down-hole setting, establishing thereby one of the criteria for evaluation in selecting a formation suitable for fracturing.

3. Prior Art

The subject of rock failure has been the focus of attention of geologists and engineers for many decades. Phenomenological failure criteria describing rock failure and breakage have been developed and used successfully in most engineering and mining applications. Examples of such criteria include specimen maximum compressive and tensile strength and the like. In rock study it has heretofore generally been assumed that rock specimens are formed from uniform homogeneous materials and have not involved a study of the actual stress conditions that affect rock fracture as that rock specimen exists in nature. However, in recent years studies relating to fracturing of wells for increasing production thereof have attempted to establish the subsurface conditions that affect crack extension during rock failure. Such studies have provided promise of techniques for improving fracture efficiency for increasing energy and minerals production from an existing source. As an example of some of the work done in the area of well fracturing, one of the co-inventors hereto, Arfon Harry Jones, is a co-inventor of a Process for Direct Measurement of the Orientation of Hydraulic Fractures covered in a recently issued U.S. Pat. No. 4,044,828 which patent involves a process for determining the direction of fracture induced hydraulically into a well bore and is cited herein as an example of a process involving hydraulically fracturing a well bore.

A field of study has heretofore been undertaken in analyzing rock fracturing, which studies the process of the present invention builds upon, involving the use of linear elastic fracture mechanics in calculating a materials fracture toughness. Such studies have occasioned investigations by a number of authorities who have investigated the conditions affecting and what occurs during a massive hydraulic fracture of rock in its natural state. An example of such an investigation is demonstrated by a paper by Secor and Pollard entitled, "On the Stability of Open Hydraulic Fracture in the Earth's Crust," as reported in, GEOPHYSICS RESEARCH LETTERS, 2, No. 11, page 510 through 513, 1975. Such investigations have established that, from the point of view of fracture mechanics, a better understanding of fracture initiation and growth during rock fracturing is achieved if fracture toughness, i.e., a measure of the rock resistance to crack extension, is first determined. Which fracture toughness determination is, of course, the subject of the process of the present invention.

Several earlier investigations, from which investigations the process of the present invention was developed, have taken the approach of requiring a first determination of fracture toughness for analysis of a geologic material. Such approach is shown in a paper by Schmidt, R. A., and Huddle, C. W. entitled, "The Effect of Confining Pressure on Fracture Toughness of Indiana Limestone," that was included in the proceedings of the 17th U.S. Symposium of Rock Mechanics, held at Snowbird, Utah, in August of 1976; and fracture toughness was considered in both a paper by Barker, L. M., entitled, "A Simplified Method of Measuring Plane Strain Fracture Toughness," that appeared in a publication entitled, ENGINEERING FRACTURE MECHANICS, 1977; and in a paper by Clifton, R. J., Simson, E. R., Jones, A. H., and Green, S. J., entitled, "Determination of Critical Stress Intensity Factor $K_{Ic}$ in a Circular Ring," that was published in, EXPERIMENTAL MECHANICS, 16, pages 233 through 238, 1976.

The present invention, similar to the burst test technique shown in the above cited article by Clifton, et al., 1976, provides for determining the fracture toughness of a specimen by internally pressurizing to fracture that thick walled cylindrical specimen, but additionally, and distinguishing the process of the present invention therefrom, it also includes subjecting the specimen to horizontal containment pressure while simultaneously pressurizing the pore fluid in the specimen, which pressurizing scheme is critical to the success of the test to obtain a specimen fracture toughness measurement that truly simulates that of the specimen it would exhibit in a down-hole situation.

Within the knowledge of the inventors, the process of the present invention has not heretofore been known or in use, and is believed therefore to be both novel and unique.

SUMMARY OF THE INVENTION

It is the principle object of the present invention to provide a process for accurately evaluating, in a laboratory setting, the fracture toughness of a specimen as that specimen would exhibit if it were part of a strata surrounding a well bore.

Another object of the present invention is to provide a process for determining, in a laboratory setting, the fracture toughness of a specimen material as it would exhibit located beneath the ground surface surrounding a well bore with the pores in that specimen saturated with fluid under pressure.

Still another object of the present invention is to provide a procedure for aiding in selecting a well bore suitable for fracturing, preferably hydraulically, to increase the production of an existing source of hydrocarbons, natural gas or water.

The steps involved in practicing the method of the present invention for determining the fracture toughness of a specimen, involve the preparation of a specimen by forming a center longitudinal bore in a cylindrical rock specimen leaving a thick wall therebetween. Within that longitudinal bore the specimen is longitudinally prenotched to bisect the bore, and a liner must be installed therein for keeping the notch faces traction free throughout the test. The liner prohibits a loading fluid from reaching the crack faces. If, however, pore fluidization of the specimen is desired to better simulate down-hole conditions, the notch faces will be loaded by the same amount of pore pressure. The specimen can then be internally and externally loaded by introducing a fluid under pressure, into the longitudinal bore, and applying external pressurization thereto, raising the internal and external pressures to maintain a desired pressure ratio until the fracture occurs at a maximum internal fluid pressure. The measured maximum internal fluid pressure can then be used to determine the test stress intensity factor of the specimen, from which determination, and considering the specimen geometry, the fracture toughness thereof can be determined.

A simulation of actual down-hole conditions includes the application of external pressure to the specimen during internal pressurization thereof, the present invention demonstrating that axial stresses exerted on the specimen can be ignored. Providing the internal pressurization of the specimen and external pressure exerted thereon are raised simultaneously maintaining a desired constant relationship therebetween, from a measurement of the pressure required to fracture the specimen and considering the specimen geometry only, the specimen fracture toughness can be determined. While obviously in a down-hole situation the horizontal stress would not vary, by selecting an appropriate ratio relationship an external stress at the point of fracture that is proximate to down-hole conditions affecting the fracture toughness of the rock wherein the well bore is drilled can be obtained. As stated above the present invention demonstrates that, in computing the specimen fracture toughness of a material as it would exhibit in an in situ state, axial stresses exerted thereon can be ignored, with the fracture toughness thereof affected only by the horizontal stresses exerted thereagainst.

A practical application for the process of the present invention involves, in selecting a well or well bore for fracturing, a consideration of the horizontal stresses the rock formation experiences at a particular well bore depth whereat fracture will be undertaken. As shown by practicing the process of the present invention, the horizontal stresses exerted on the material around a well bore are of paramount consideration and vertical stresses thereon can be ignored in determining whether the fracturing of formation surrounding a well is economically practical. Therefore, the present invention also provides for optimumly selecting a formation wherein a well bore is formed that is suitable for hydraulic fracturing where, at a depth in that well bore whereat fracture is to be undertaken, the horizontal stresses exerted on the rock formation surrounding that well bore depth are known or can be calculated or estimated.

Other objects and steps in practicing the method of the present invention will be further elaborated on hereinafter and will become more apparent from the following detailed description, taken together with the accompanying drawings.

THE DRAWINGS

FIG. 1, is a profile sectional view of a cylindrical specimen of rock material arranged for testing between end caps that are sealed thereto, the specimen having a longitudinal center bore formed therein that is arranged and appropriately connected to receive fluid under pressure;

FIG. 1(a), a graphic representation of the stress intensity factor for examples of jacketed cylindrical rock specimens relating to certain crack lengths developed therein;

FIG. 1(b), a graphic representation of the stress intensity factor for examples of unjacketed cylindrical rock specimens relating to certain crack lengths developed therein;

FIG. 2, a schematic of a well bore and the materials therearound showing, with arrows indicating the internal and external pressures exerted thereon at the time of fracturing;

FIG. 3(a) through 3(d) are schematic representations of a rock specimen, each showing the specimen subjected to internal pressurization to fracture thereof, representations (a) and (b) showing the specimen subjected to confining pressure, the pores of the specimen in (b) shown with arrow $P_p$ as being subjected to fluid under pressure;

FIG. 4, a graph comparing rock specimen internal pressurization with crack length during incipient crack growth for a sample that is subjected also to a confining pressure;

FIG. 5, a graph comparing the specimen stress intensity factor for a cylindrical rock specimen with cracked growth where a constant relationship of confining pressure over internal pressure is maintained during pressurization; and FIG. 6, a chart showing experimental test results involved with fracturing of specimens cut from Indiana limestone.

DETAILED DESCRIPTION

Figure 1:
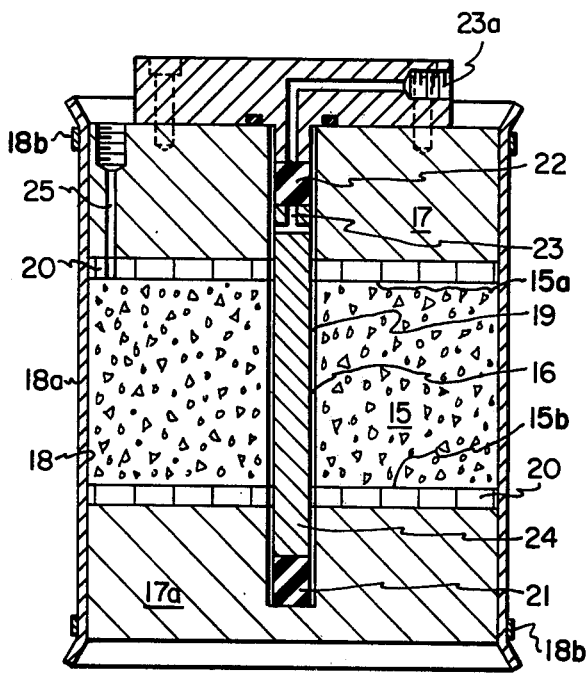

Referring now to the drawings:

The practice of the process of the present invention is founded on certain generally accepted assumptions that are well recognized in the practice and theory of linear elastic fracture mechanics. Such assumptions deal with homogeneous materials and therefore may not exactly reflect the actual composition, make up, or the like, of a rock medium around a well bore at a certain depth beneath the ground surface. They are, however, useful for constructing a theoretical model from which to predict, in a laboratory setting, what will occur to that rock medium during fracture thereof. Therefore, while the following assumptions may not exactly reflect actual conditions they are essentially correct and will be used as a basis for demonstrating the practice of the process of the present invention.

A first assumption in the practice of the process of the present invention is that the rock medium under test is composed of one or more homogeneous isotropic layers. Further, the present invention assumes that the mode of failure of that rock is elastic brittle fracture; i.e., the material will behave elastically during the loading process until catistrophic separation of crack surfaces occurs. This assumption supposes that the size of the inelastic zone at the crack tip is considerably smaller than any other geometric length in the surrounding medium, and hence, the stress field around the crack tip is anticipated to exhibit a square root singularity. This stress singularity, hereinafter identified as $K_I$, is also the stress intensity factor (SIF) due to the applied loads and geometry of the specimen. While it should be realized that such a stress singularity is physically impossible, it is mathematically convenient since the value of $K_I$ controls the local deformation field around the crack tip. Further, it is well known that within the context of elastic fracture mechanics or small scale yielding situations the stress intensity factor is or will be related to such physical quantities as energy release rates or surface energy of the fractured material. A commonly accepted axiom known as the Griffith Fracture Criteria, reported in a 1920 publication entitled, "The Phenomena of Rupture and Flow in Solids," Phil. Trans, Royal Society, London, Series A, 221, 163–168, and expanded upon by G. R. Irwin in his article entitled, "Fracture Mechanice," published in a book entitled, "Structural Mechanics" by Poyanion Press in 1960, states that: "An existing crack in a body will extend as long as the rate of decrease of the potential energy of the cracked body is greater than or equal to a critical value." Expressing the above in terms of stress intensity factor, a crack will extend if the $K_I$ is greater than or equal to $K_{Ic}$, where $K_I$ is as defined above and $K_{Ic}$ should be understood to be and is hereinafter referred to as the specimen fracture toughness and is a material property evaluated experimentally. The fracture toughness $K_{Ic}$ and its experimental derivation to simulate subsurface conditions is, of course, the subject matter of the process of the present invention.

The fracture toughness $K_{Ic}$ of a material as it would exhibit in its natural setting beneath the earth's surface determines the amount of pressure exerted on a face thereof that is required to initiate and continue a crack in that material, and so is critical to well bore fracturing as the fluid pressure in the well bore required to initiate and continue a fracture, or the stress intensity factor $K_I$, must be continually greater than or equal to the material's fracture toughness $K_{Ic}$. Fracture or crack progress would halt when the $K_I$ becomes less than the $K_{Ic}$. Therefore, to select a formation containing a well bore suitable for fracturing, the fracture toughness of the rock surrounding that well bore at the depth where fracture is to be undertaken needs to be considered. Practicing the process of the present invention provides for a determination of the fracture toughness of the material surrounding a well bore from a knowledge of the rock's stress intensity factor and the horizontal stresses thereon. Also the present invention demonstrates that, in planning fracturing of a well bore to increase production, the vertical stresses exerted at the depth of that fracture need not be considered.

The present invention therefore not only provides an experimental procedure for determining the fracture toughness of a rock specimen material in a laboratory setting as it would exhibit in a field situation, it also provides criterion for selecting a formation containing a well bore suitable for fracturing from an analysis of the horizontal stresses at a desired fracture depth and the composition of the material surrounding that well bore only.

Figure 2:
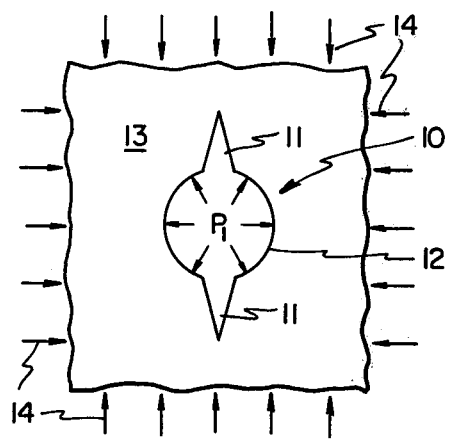

FIG. 2 shows a schematic overview of a well bore 10 in a geologic material 13 that has been subjected to internal pressurization, identified as $P_i$, which pressure is shown to have induced cracks 11 therein at 180° intervals from one another within that geologic material 13 surrounding the well bore circumference 12. Geologic material 13, it should be understood, is below ground level and therefore experiences both horizontal and vertical stresses. Shown in FIG. 2, Arrows 14 indicate such horizontal stresses with, it should be understood, vertical stresses, not shown, being also applied thereon. While not shown, as the well bore 10 is, in its natural state, exposed to fluid under pressure, it should be assumed that the pores of the geologic material 13 will be saturated, the presence of which fluid is preferably considered in determining the fracture toughness of that material in its natural state. Therefore, from the schematic of FIG. 2, it should be obvious that to fracture geologic material 13 by introduction of a pressure medium $P_i$ into well bore 10, the stresses and conditions exerted on and affecting the rock surrounding that well bore in its natural state need to be considered in determining the fracture toughness of that geologic material. As will be shown hereinbelow, the factors that affect the geologic material surrounding a well bore are taken into account by the process of the present invention, which process therefore provides for a laboratory reproduction of the conditions that a specimen experiences if it were deep under the ground and therefore provides for a determination of the in situ fracture toughness of a particular geologic material.

The process of the present invention involves, in a laboratory setting, steps and procedures performed on a specimen 15, shown in FIG. 1, that is preferably cylindrical in shape having a longitudinal bore 16, hereinafter referred to as bore, formed therein, leaving a thick wall between the bore 16 circumference and the specimen 15 circumference. The specimen 15 is preferably loaded internally by introduction of a fluid under pressure, $P_i$, into bore 16, the fluid pressure therein to be increased to a peak value whereat the specimen fractures as shown in the schematic of FIG. 2. Whereafter, from that peak pressure and taking into account certain constants and measurements, we will be outlining later herein, the fracture toughness of the specimen material can be calculated. To induce fracture occuring along a predetermined line through the specimen, the bore 16 is preferably prenotched along its length at points approximately 180° across from one another utilizing a diamond impregnated wire, or the like, not shown.

Figure 1A:
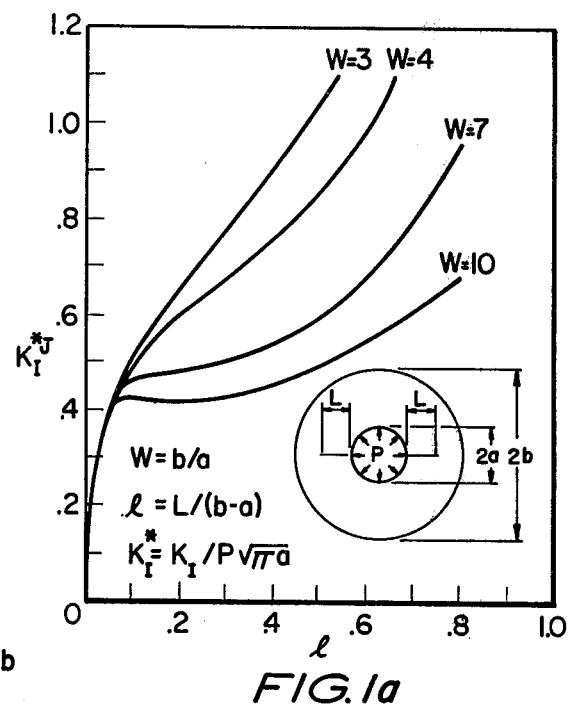

As shown in FIG. 1, to perform the laboratory process of the present invention, specimen 15 is preferably arranged between end caps 17 and 17(a) that are formed from steel, or a like rigid material, whose deformation will be minimal when subjected to pressurization. The specimen in one test configuration preferably has an outer jacket 18 formed of a urethane or the like arranged around it. That outer jacket 18 is preferably maintained against to the specimen by external pressurization and held together by metal bands 18(b), or the like, arranged therearound, holding the outer jacket 18 to the specimen 15 keeping it fluid tight. To keep the specimen interior dry, bore 16 preferably is lined with an inner jacket 19 such as one made from Tygon or a like material, to prohibit the passage of fluid into the specimen 15. Fluid tight seals 20 are preferably arranged between the specimen ends 15(a) and 15(b) and the end caps 17 and 17(a) that should be understood to be preferably constructed of a vinyl, or a like material. The bottom steel end cap 17(a) is provided with end plug 21, preferrably formed of rubber, to prohibit passage of fluid out from bore 16 and a top plug 22 is arranged in end cap 17. Top plug 22 has a pressure inlet pipe 23 fitted therethrough that is connected at its end 23(a) to a source of fluid under pressure, not shown. To limit the volume of fluid needed to be admitted into bore 16 to fracture the specimen 15, a steel rod 24 of lesser diameter than the circumference of bore 16 is preferrably arranged therein, reducing, thereby, the area within the bore needed to be filled with fluid under pressure to fracture the specimen 15. The jacketed specimen 15 configuration shown in FIG. 1, preferrably also involves a pressure release port 25, or a like pressure release safety device, arranged with the end cap 17 for providing for a controlled passage of fluid out from the top of the specimen 15 after fracture. So arranged the specimen can be internally pressurized, admitting fluid under pressure into bore 16 from a pressure source, not shown, through pressure inlet 23(a). Such fluid pressure is increased until the specimen fractures at a maximum pressure whereafter, using this maximum pressure, $P_{imax}$, the stress intensity factor $K_I$ can be calculated from the formula $K_I = K_I^{*J}(l,w) P_{imax} \sqrt{\pi a}$ where $K_I^{*J}$ is a non-dimensional function of the jacketed specimen that can be determined by the picking off of its value from the graphic representation of FIG. 1(a). Which graph of FIG. 1(a) was formulated analytically and is contained in an article by Bowie, O. L., and Freese, D. E., entitled, "Elastic Analysis for Radial Crack in a Circular Ring," published in ENGINEERING FRACTURE MECHANICS, 4, page 315, 320, 1972. l is the non-dimensional crack length, as defined by $L/(w-1)a$, with L being the actual length, w the ratio of the outer to the inner radius of the specimen 15, and a is the radius of bore 16. Of course, $P_{imax}$ is the measured maximum pressure exerted within bore 16 and $\pi$ is a constant 3.1416. Obviously, the above computation does not involve application of either horizontal or vertical stresses to the specimen which stresses application will be covered in detail later herein. For the specimen of Indiana limestone, FIG. 6, tests numbers 1 through 5 reflect specimen internal pressurization to fracture and involve negligable vertical stress application thereto.

With $K_I^{*J}$ as a function of l for defined wall thickness ratios, the fracture toughness $K_{Ic}$ of the material can be calculated without reference to the measurement of the crack length developed. Therefore, the value of the maximum internal pressure $P_{imax}$ prior to catastrophic failure of the specimen 15, is the only measurement needed to compute the specimen fracture toughness. The value of the fracture toughness $K_{Ic}$ for the jacketed specimen 15 is therefore given by the equation: $K_{Ic} = \overline{K}_I^{*J} P_{imax} \sqrt{\pi a}$ where $\overline{K}_I^{*J}$ is the local minimum value of $K_I^{*J}$ for the given value of w.

Of course, as stated earlier herein, a formation surrounding around a well bore, located below the earth's surface would experience both vertical and horizontal stresses thereon and the pores thereof would possibly be fluidized to a point of saturation. With this in mind, and utilizing the specimen 15 configuration shown in FIG. 1, to simulate down-hole conditions, the above procedure could be undertaken inside a pressure vessel or chamber, not shown, or the like, where controlled vertical and horizontal stresses could be applied to that specimen 15 simultaneously to internal pressurization thereof by passing, as described, fluid under pressure into bore 16, and, to more exactly simulate down-hole conditions, the specimen can also be subjected to a pore saturation, so as to pass fluid under pressure into the specimen 15 between the inner jacket 19 and the outer jacket 18 such that when the specimen is subjected to internal and external fluid under pressure and the pores thereof will be pressurized. Such pore pressurization is shown in tests numbers 9 through 12 of FIG. 6, these tests compared to the other tests demonstrating that pore pressurization only increases the maximum pressure $P_{imax}$ (required to fracture an Indiana limestone specimen by the value of the pore pressure, $P_p$.) So, while pore pressurization would more accurately simulate down-hole conditions, its inclusion would not alter the formula for calculating the specimen fracture toughness as long as the absolute pressure $P_{imax}$ is replaced by the effective pressure $P_{imax} - P_p$, where $P_p$ is the pore pressure.

Figure 3:
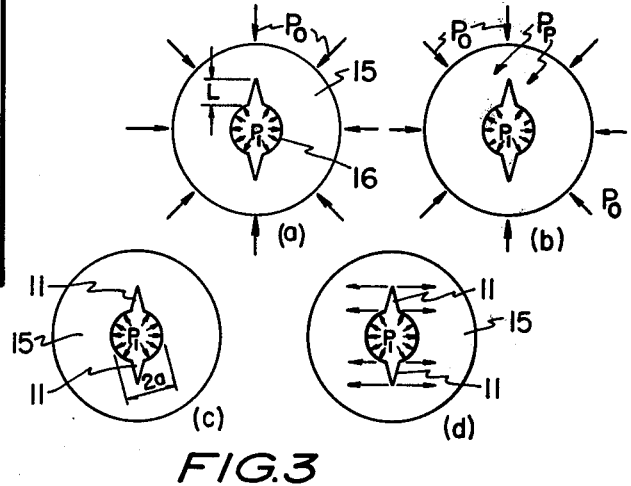

Turning to FIGS. 3(a), through 3(d), in FIG. 3(c) is shown an unconfined specimen 15 with internal pressurization exerted therein producing cracks 11, with, in FIG. 3(d) that internal pressurization shown exerting force within the cracks 11 to further pry the specimen apart.

FIG. 3(a) shows the specimen 15 configuration of FIG. 3(c) subjected also to confining or horizontal stresses, with FIG. 3(b) showing the specimen 15 of FIG. 3(a) subjected to pore pressurization to saturation, shown as arrows $P_p$. FIGS. 3(a) through 3(c) therefore show pictorially the different conditions the specimen 15 may be subjected to in practicing the method of the present invention.

Figure 1B:
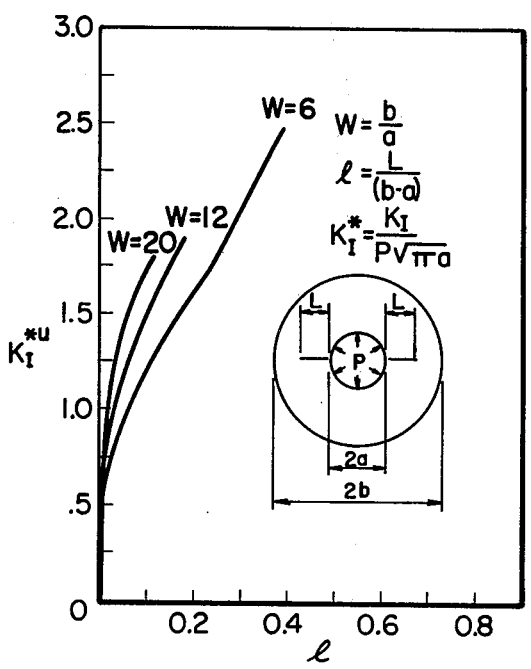

With specimen 15 arranged in an appropriate pressure vessel or chamber, both horizontal and axial pressures including pore pressurization, as desired, acting thereon can be applied to simulate an in situ state of stress that the specimen would experience in a down-hole situation. So arranged, the stress intensity factor, $K_I^c$, for the specimen in a chamber, can be obtained by the principle of superposition, as relating to FIGS. 3(a) through 3(d). That principle of superposition being, that under appropriate boundary conditions, an elastic problem can be broken into the sum of several problems, the sum of whose solutions is the solution of the original problem.

$$K_I^c = (P_i - P_p)\sqrt{\pi a} K_I^{*J} - (P_o - P_p)\sqrt{\pi a} K_I^{*u}$$

with $P_o$ the pressure applied to the outside of specimen 15 and $K_I^{*u}$ is a non-dimensional stress intensity factor of an unjacketed specimen as determined from an inspection of the graph of FIG. 1(b). Therefore:

$$K_I^{*c} = K_I^{*J} - (P_o - P_p)/(P_i - P_p) K_I^{*u}$$

$K_I^{*c}$ is, as defined, the non-dimensional stress-intensity factor for a sample subjected to confining pressure. Therefore, the above equation indicates that for some fixed value of $P_o$, $P_p$ and $P_i$ the stress intensity factor, $K_I^c$ at the cracked tip will decrease with increasing crack growth. Under such conditions, such crack growth will always be stable. Therefore, the relationship between $P_i$ and L at incipient crack growth under constant confining and pore pressure can be obtained by substituting $K_I^c$ equal to $K_{Ic}^c$ and rearranging the above equation to:

$$\overline{P}_i^* = (P_i - P_p)\sqrt{\pi a}/K_{Ic}^c = [1 + (P_o - P_p)\sqrt{\pi a} K_I^{*u}/K_{Ic}^c]/K_I^{*J}$$

Figures 4, 5, 6:
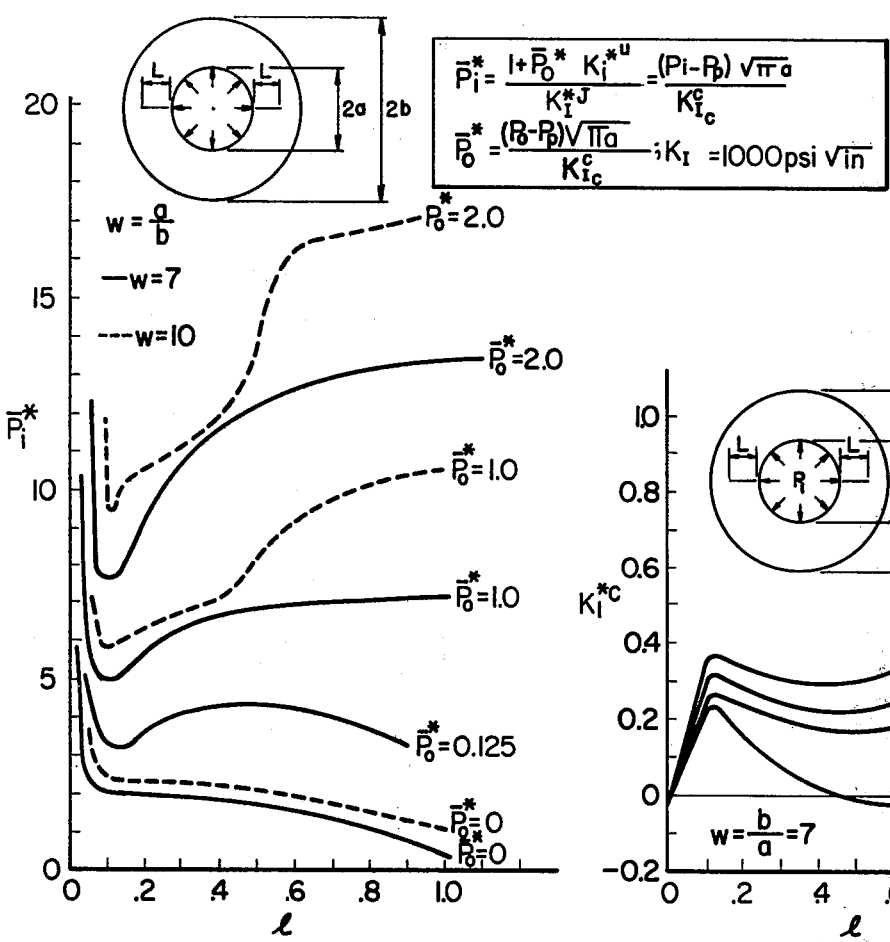

In FIG. 4 is shown the relationship between $\overline{P}_i^*$ and the l curve for the different values, $\overline{P}_o^*$ is equal to $(P_o - P_p)\sqrt{\pi a}/K_{Ic}^c$, $P_i^*$ and $P_o^*$ being non-dimensional internal and external pressures respectively, with $K_{Ic}^c$ as stated above, being the fracture toughness under confining pressure. Shown in FIG. 4, for each effective particular external pressure $P_o-P_p$, the effective internal pressure, $P_i-P_o$, required to produce incipent crack growth as changed. The curves of FIG. 4, that represent data produced analytically, indicate that, where a specimen like specimen 15 is subjected to a constant confining pressure, crack growth will be stable throughout, and therefore, to calculate $K_{Ic}{}^c$, a precise knowledge of the crack length at a specific $P_i$ would be essential. However, in reference to FIG. 5, where proportional loading conditions are undertaken during experimental fracture, i.e., in a procedure undertaken on a specimen like specimen 15 where a fixed ratio of outer to inner pressure $\bar{P}_o{}^*/\bar{P}_i{}^*$ is held constant, the value of $K_{Ic}{}^c$ is obtained from the relationship:

$$K_{Ic}{}^c = (P_{imax} - P_p)\sqrt{\pi a}\bar{K}_I{}^{*c}$$

where $K_I{}^{*c}$ is the value of the local minimum stress intensity factor for given values of w and $(P_o-P_p)/(P_i-P_p)$. Therefore, the $K_I{}^{*c}-1$ relationship can be expressed in the form:

$$K_I{}^{*c} = K_I{}^{*J}(l,w) - (P_o-P_p)/(P_i-P_p)K_I{}^{*u}(l,w)$$

where $\bar{K}_I{}^{*c}$ is the value of the local minimum stress intensity factor of the function shown in FIG. 5 for specific ratio of w. Which w, as defined earlier herein, is the ratio of outer to the inner radius of specimen 15 and $(P_o-P_p)$ over $(P_i-P_p)$ is a constant. The $K_I{}^{*c}$ can therefore be determined from the graph of FIG. 5. The fracture toughness of the confined specimen $K_{Ic}{}^c$ is therefore equal to $K_I{}^{*c}[(P_{imax}-P_p)\sqrt{\pi a}]$.

As provided in the above discussion relating to arriving at fracture toughness of a confined specimen, $K_{Ic}{}^c$ is equal to $\bar{K}_I{}^{*c}[(P_{imax}-P_p)]\sqrt{\pi a}$ and, allowing that $K_I{}^{*c}$ can be arrived at by maintaining the constant relationship of $(P_o-P_p)/(P_i-P_p)$ at some fixed constant of $(P_o-P_p)/(P_i-P_p)$, therefore, then the fracture toughness of the specimen 15 can be determined directly from a consideration of the actual $P_{imax}$ at specimen fracture, taking into account, of course, the specimen geometry. It should here be noted that, as with the earlier discussion relating to a jacketed specimen, the above formula does not consider axial stresses applied to such specimen. That such axial stresses need not be considered has been established experimentally as reflected by the chart of FIG. 6, wherein are summarized tests made on both confined and unconfined specimens of Indiana limestone. Indiana limestone being an example of a medium to high permeability rock that is suitable for practicing the process of the present invention at low loading rates. These tests were undertaken as shown, under different conditions, determining thereby the $K_I$ and $K_{Ic}$ of a specimen, these results supporting the formulas heretofore disclosed herein. Comparing the tests of FIG. 6, tests numbers one through five are reflective of a small axial stress with tests 6 through 12 showing an axial stress ten times greater with the fracture toughness of the specimens remaining essentially the same. A comparison of these test results therefore demonstrates that axial stresses can be discounted in determining specimen fracture toughness by the present method. However, tests 16 through 18 demonstrate that, where confining pressure was applied to a specimen there was a marked increase in fracture toughness of approximately 80% over the fracture toughness of an unconfined specimen. Therefore, the test results shown in FIG. 6 demonstrate that while axial stresses can be ignored, in computing specimen fracture toughness of a specimen horizontal stresses exerted thereon need be considered. The formulas as presented herein are therefore supported by the test results of FIG. 6, those formulas therefore providing a procedure for computing, in a laboratory setting, the fracture toughness of a rock specimen as it would exhibit in a down-hole situation.

The test results of FIG. 6 also demonstrate that axial stresses of a rock strata surrounding a well bore in its natural state can also be ignored in calculating in situ fracture toughness. As stated earlier herein, when pore pressurization is applied to the specimens of tests numbers 9 through 12, the fracture toughness of the specimen was not affected. Rather as the specimen is subject to internal pressurization $P_i$ the pore fluid pressurization $P_p$ is equal to, and the same as, the confining pressure $P_o$. Therefore, and in concert with the effective stress value theory, the above disclosed formulas are not altered by pore pressurization.

While the above described steps are preferred in practicing the process of the present invention, it should be understood that modifications, and to changes, substitutions, or addition of another step or steps that would be obvious from the present disclosure could be made without departing from the scope or spirit of the disclosure of the present invention, which scope or spirit is encompassed in the following claims which claims we consider to be our invention.

We claim:

1. A process for measuring the fracture toughness of rock under simulated downhole stress conditions including the steps of, preparing a section of rock appropriately to have a cylindrical shape and a center longitudinal bore formed therethrough producing thereby a thick walled specimen;

longitudinally prenotching that longitudinal bore appropriately such that, when sufficiently pressurized, specimen fracture will occur at said prenotching to bisect said specimen;

arranging said specimen appropriately between end caps that will deform minimally when subjected to pressurization, closing off thereby said longitudinal bore;

lining said longitudinal bore with fluid tight jacket, pressurizing internally said longitudinal bore and incrementally raising that internal pressure until specimen fracture occurs;

applying confining pressure to said specimen simultaneously to apply internal pressurization thereto, which internal and confining pressures are maintained at a constant ratio until specimen fracture occurs;

measuring the maximum pressure within said longitudinal bore at the time of specimen fracture; and calculating from the measured maximum pressure, the specimen fracture toughness taking into account the specimen geometry.

2. A process as recited in claim 1, further including the steps of installing a fluid tight jacket around the specimen;

lining the specimen longitudinal bore with a fluid tight liner; and sealing the specimen ends against fluid passage.

3. A process as recited in claim 1, further including the step of, installing a non-compressable member within the longitudinal bore, taking up a portion of the volume therein.

4. A process as recited in claim 1, wherein the fracture toughness of a specimen subjected to confining pressure, $K_{Ic}{}^c$, with the ratio of the confining effective pressure $(P_o-P_p)$ divided by the internal effective pressure, $(P_i-P_p)$, held constant, is calculated by, multiplying the stress intensity factor of the confined specimen $\overline{K}^{*c}$ by the maximum effective internal pressure, $(P_{imax}-P_p)$ times the square root, $\sqrt{\ }$, of $\pi$ times the radius of the longitudinal bore, a, or:

$$K_{Ic}{}^c = \overline{K}_I{}^{*c}\,[(P_{imax}-P_p)]\sqrt{\pi a}$$

5. A process as recited in claim 1, wherein with pore pressurization maintained at zero, the fracture toughness of a specimen subjected to confining pressure, $K_{Ic}{}^c$, with the ratio of confining effective pressure, $P_o$, divided by the internal effective pressure, $P_i$, held constant, is calculated by, multiplying the stress intensity factor of the confined specimen $\overline{K}^{*c}$ by the maximum effective internal pressure, $P_{imax}$, times the square root, $\sqrt{\ }$, of $\pi$ times the radius of the longitudinal bore, a, or:

$$K_{Ic}{}^c = \overline{K}^{*c}(P_{imax}\sqrt{\pi a})$$

* * * * *